United States Patent
Shealy

(12) 
(10) Patent No.: US 6,751,506 B2
(45) Date of Patent: Jun. 15, 2004

(54) ELECTRICAL STIMULATION TO REDUCE FREE RADICAL LEVELS

(76) Inventor: C. Norman Shealy, Route 1, Box 216, Fair Grove, MO (US) 65648

( * ) Notice: Subject to any disclaimer, the term of this patent is extended or adjusted under 35 U.S.C. 154(b) by 238 days.

(21) Appl. No.: 10/154,334

(22) Filed: May 23, 2002

(65) Prior Publication Data

US 2003/0220668 A1 Nov. 27, 2003

(51) Int. Cl.$^7$ ................................................ A61N 1/08
(52) U.S. Cl. ........................................ 607/68; 128/898
(58) Field of Search .............................. 607/2, 68, 69, 607/76, 50; 128/898

(56) References Cited

U.S. PATENT DOCUMENTS

| | | |
|---|---|---|
| 5,109,847 A | 5/1992 | Liss et al. |
| 5,609,617 A | 3/1997 | Shealy et al. |
| 6,023,642 A | 2/2000 | Shealy et al. |
| 6,233,489 B1 | 5/2001 | Shealy et al. |

OTHER PUBLICATIONS http:/www.life–enthusiast.com/twighlight/shealy/ring-s.htm—website printout , Mar. 5, 2004, 5:21 pm.*
http:www.normshealy.net/curriculum.htm —website printout, Mar. 6, 2004, 5:42 pm.*
Liss Cranial Stimulator—Professional Instrument Manual, 1994, pp. 1–11.*

* cited by examiner

*Primary Examiner*—Mark Bockelman
(74) *Attorney, Agent, or Firm*—Foley & Lardner

(57) ABSTRACT

The endogenous enhancement of antioxidants in a human being has the ability to reduce free radicals. Free radicals are linked to cell damage associated with aging and a wide variety of diseases. Exogenous administration of antioxidants has safety risks given that appropriate dosage levels are uncertain. Furthermore, some individuals taking rather large doses of antioxidants still have evidence of significant free radical production. The present invention provides the benefits of antioxidants through electrical stimulation that increases endogenous antioxidant levels without the need for exogenous supplements.

13 Claims, 5 Drawing Sheets

CARRIER FREQUENCY
15,000 hz MONOPOLAR

1st MODULATOR
15 hz   FIG. 3B

2nd MODULATOR
500 hz   FIG. 3C

TYPICAL COMBINED
WAVEFORM (MONOPOLAR)

TYPICAL COMBINED
WAVEFORM (BIPOLAR)

ELECTRICAL STIMULATION TO REDUCE FREE RADICAL LEVELS

FIELD OF THE INVENTION

This invention pertains to a method for enhancing antioxidant levels in human beings without administration of exogenous antioxidants through diet or supplements.

BACKGROUND OF THE INVENTION

Oxidative stress is thought to be involved in the aging process in aerobic organisms and to play a role in the pathogenesis of several disease states, including Alzheimer's disease, myocardial infarction, atherosclerosis, Parkinson disease, autoimmune diseases, radiation injury, emphysema, sunburn, glomerular disorders, schizophrenia, sickle cell disease, leukemia, osteoporosis, infertility, cancer, retinopathy, and noise-related hearing impairment. Oxidative stress is the result of free radicals, such as the hydroxyl radical, reacting with biological macromolecules, such as lipids, proteins, nucleic acids and carbohydrates. The initial reaction generates a second radical, which in turn can react with a second macromolecule to continue the chain reaction. In the process of reacting, a free radical can modify protein or DNA structures, disrupt individual nucleotide bases, and thereby cause effects such as single-strand breaks and cross-linking in nucleic acids. Free radical-induced oxidative stress has been associated with a number of major cardiovascular disease risk factors. See "Reactive Oxygen Species (ROS)" (first printed in R & D Systems' 1997 Catalog), available at http://www.rndsystems.com/asp/g_sitebuilder.asp?bodyId=222.

A current theory holds that free radical-induced oxidative stress is a major factor in the long-term tissue degradation associated with aging. This free radical theory proposes that aging is the cumulative result of oxidative damage to the cells and tissues of the body that arises primarily as a result of aerobic metabolism. Several lines of evidence have been used to support this hypothesis including the claims that: (1) Variation in species life span is correlated with metabolic rate and protective antioxidant activity; (2) enhanced expression of antioxidative enzymes in experimental animals can produce a significant increase in longevity; (3) cellular levels of free radical damage increases with age; and (4) reduced calorie intake leads to a decline in the production of free radical and an increase in life span. The free radical theory may also be used to explain many of the structural features that develop with aging including the lipid peroxidation of membranes, formation of age pigments, cross-linkage of proteins, DNA damage and decline of mitochondrial function. Wickens, A. P., "Ageing and the free radical theory," Respir. Physiol., Vol. 128(3), pp. 379–91 (2001).

Free radicals only occur in trace quantities in biological tissues and are extremely reactive. Because of the difficulty of directly measuring free radicals in vivo, measurements can be made using biomarkers, for example, an assay of antioxidant vitamins and free radical scavengers. Therefore, oxidative stress has been mainly observed through such indirect biomarkers of free radical-induced damage. In aerobic organisms, oxidative damages to tissues and organs is prevented by a network of defenses which include antioxidant and repairing enzymes, as well as small molecules with scavenging ability, such as antioxidant vitamins. For these reasons, the assay of antioxidant vitamins and of small molecular free radical scavengers in biological milieus may be used, if appropriately performed, to quantify the defense status against oxidative damage and to provide an indirect estimate of free radical production in aging humans. Polidori, M. C., et al., "Peripheral non-enzymatic antioxidant changes with human aging: a selective status report," Biogerontology, Vol. 2(2), pp. 99–104 (2001).

Malondialdehyde (MDA) levels both in blood and urine have been one of the most widely used free radical markers. Measurement of MDA excretion in the urine became available in 1964. MDA is the end product of lipid peroxidation, and this urinary calorimetric assay represents by far the simplest approach to measurement of free radical activity. Furthermore, this colorimetric assay has been highly statistically significantly correlated with the fluorometric approach.

Mammalian cells possess elaborate defense mechanisms to detoxify radicals. Radical-scavenging antioxidants (e.g., vitamin E) interrupt the chain by capturing the radical; the vitamin E radical is relatively stable, and it can be enzymatically converted to its non-radical form. Excessive amounts of cellular oxidants, which animal cells constantly produce, can induce oxidative damage. Cellular antioxidants provide a defense against the damaging effects of the cellular oxidants. However, in moderate concentrations, cellular oxidants are necessary for a number of protective reactions which eliminate cancerous and other life-threatening cells, such as anti-microbial phagocytosis and apoptosis. Excess antioxidants could inhibit the protective anti-cancer function that the apoptosis process provides. Abundant antioxidants might suppress these protective functions, particularly in people with a low innate baseline level of cellular oxidants. Salganik, R. I., "The benefits and hazards of antioxidants: controlling apoptosis and other protective mechanisms in cancer patients and the human population," J. Am. Coll. Nutr., Vol. 20(5 Suppl.), pp. 464S–472S (2001).

Conventional antioxidant supplements comprise, for example, vitamin C, vitamin E, beta-carotene, or other forms such as red ginseng or DHEAs, for example. Given that antioxidant supplements can actually be harmful in high doses to patients who have low levels of baseline cellular oxidants, safe antioxidant supplement use requires an accurate dosage level corresponding to each patient's needs. Each patient's baseline needs would have to be determined periodically because it is also clear that the optimal dosage of antioxidant supplements probably varies over time with each patient. Meagher, E., et al., "Antioxidant therapy and atherosclerosis: animal and human studies," Trends Cardiovasc. Med., Vol. 11 (3–4), pp. 162–5 (2001).

In healthy individuals, a delicate balance exists between the production of free radicals and the production of antioxidants. Free radicals are produced in the body as byproducts of normal metabolism and as a result of exposure to radiation and some environmental pollutants. They are normally neutralized by the body's production of antioxidant enzymes (super oxide dismutase, catalase, and glutathione peroxidase) and the nutrient-derived antioxidant small molecules (Vitamin E, Vitamin C, carotene, flavonoids, glutathione, uric acid, and taurine). In some pathological conditions, the natural balance can be upset by oxidative stress in the presence of certain diseases, such as diabetes. The oxidative stress can cause a reduction in the body's normal production of antioxidants. To prevent deterioration of antioxidant levels, it is conventionally recommended to consume adequate amounts of antioxidant-rich foods, e.g., fruits and vegetables, and also to take supplements as necessary. Sardesai, V. M., "Role of antioxidants in health maintenance," Nutr. of Clin. Pract., Vol. 10(1), pp. 19–25 (1995).

Despite the extensive research in the use of antioxidants, there is not a clear-cut consensus that these antioxidants are totally successful in reducing free radicals. Sacheck, J. M., et al., "Role of Vitamin E and Oxidative Stress in Exercise," *Nutrition*, Vol. 27(10), pp. 809–14 (2001), Meagher, E., et al., "Antioxidant Therapy and Atherosclerosis: Animal and Human Studies," *Trends Cardiovasc. Med.*, Vol. 11(3–4), pp. 162–5 (2001). Although cancer tissue has significant decreases in glutathione, vitamin C, and vitamin E, there is no evidence that taking the supplements actually prevents cancer. Skrzydlewska, E., et al., "Antioxidant Status and Lipid Peroxidation in Colorectal Cancer," *Toxicol. Environ. Health A.*, Vol. 64(3), pp. 213–22 (2001). On the other hand, there is considerable evidence that the antioxidants found in natural sources, such as vegetables and fruits, do have a beneficial effect. Trichopoulou, A., et al., "Guidelines for the Intake of Vegetables and Fruit: The Mediterranean Approach," *Int. J. Vitam. Nutr. Res.*, Vol. 71(3), pp. 149–53 (2001). Despite the lack of great clinical significance in the use of antioxidants, there is a great argument for the use of micronutrient antioxidants as a standard in many diseases, including cancer and Type 2 diabetes. It is also of some interest that the antioxidants themselves apparently do not ordinarily cross the blood brain barrier, a significant problem in reducing the known negative effects of free radicals in many degenerative central nervous system diseases, such as Alzheimer's. Blass, J. P., "Brain Metabolism and Brain Disease: Is Metabolic Deficiency the Proximate Cause of Alzheimer Dementia?" *J. Neurosci. Res.*, Vol. 66(5), pp. 851–56 (2001). Finally, an effective antioxidant supplement regimen can be expensive to maintain.

Other than antioxidants, there is only one known non-antioxidant technique for reducing free radicals. That is, 6 degrees head down bed rest; however, that can require as much as 17 days of simulated weightlessness. Furthermore, bed rest and the corresponding inactivity have also been linked to increased free radical levels. Peng, Y., et al., "Effects of Hyposi and Qigong on Urine Malondialdehyde, Superoxide Dismutase and Circulating Endothelial Cell in Humans During Simulated Weightlessness," *Space Med. Eng. (Beijing)*, Vol. 11 (2), pp. 136–8 (1998); Pawlak, W., et al., "Effect of Long Term Bed Rest in Men on Enzymatic Antioxidative Defence and Lipid Peroxidation in Erythrocytes," *J. Gravit. Physiol.*, Vol. 5(1), pp. 163–4 (1998).

It has been disclosed that treating a patient with electrical stimulation at acupuncture points known as the "Ring of Air," can endogenously increase serum neurotensin levels in living human beings. See U.S. Pat. No. 6,233,489. It has also been disclosed that treating a patient with electrical stimulation at acupuncture points known as the "Ring of Fire" can increase serum dehydroepiandrosterone (DHEA) levels. See U.S. Pat. No. 5,109,847. Until now, however, there has been no known method of reducing free radical levels in a living human being in a manner similar to the "Ring of Air" or "Ring of Fire" electrical stimulation.

SUMMARY OF THE INVENTION

The present invention provides a method for enhancing or restoring antioxidant levels in a living human being. Because antioxidants are naturally occurring in the human body, in accordance with the present invention endogenous production of antioxidants may be stimulated without requiring the use of exogenous dietary supplements or pharmaceutical preparations containing antioxidants or antioxidant analogs.

Antioxidants levels in human beings may be raised without the use of dietary supplements or pharmaceuticals by applying electrical stimulation to specific epidermal points of the individual's body for a period of time, preferably daily. The electrical stimulation is preferably applied to specific locations on the individual's body which correspond to 13 well-known acupuncture points known as the "Ring of Crystal." The electrical stimulation can be applied to these acupuncture points over a number of weeks to achieve a significant increase in antioxidant levels and a corresponding decrease in free radical activity within the patient. Preferably, electrical stimulation is applied for a minimum period of 2 to 4 weeks.

Electrical stimulation of the Ring of Crystal acupuncture points on the human body, in accordance with the present invention, has been shown to be highly efficacious among 80 percent of subjects tested in reducing free radicals, and it does not appear to risk potentially excessive antioxidants levels that may be produced by increased dosages of exogenous antioxidant supplements.

Further objects, features and advantages of the invention will be apparent from the following detailed description taken in conjunction with the accompanying drawings.

DETAILED DESCRIPTION OF THE PREFERRED EMBODIMENTS

Figure 1:
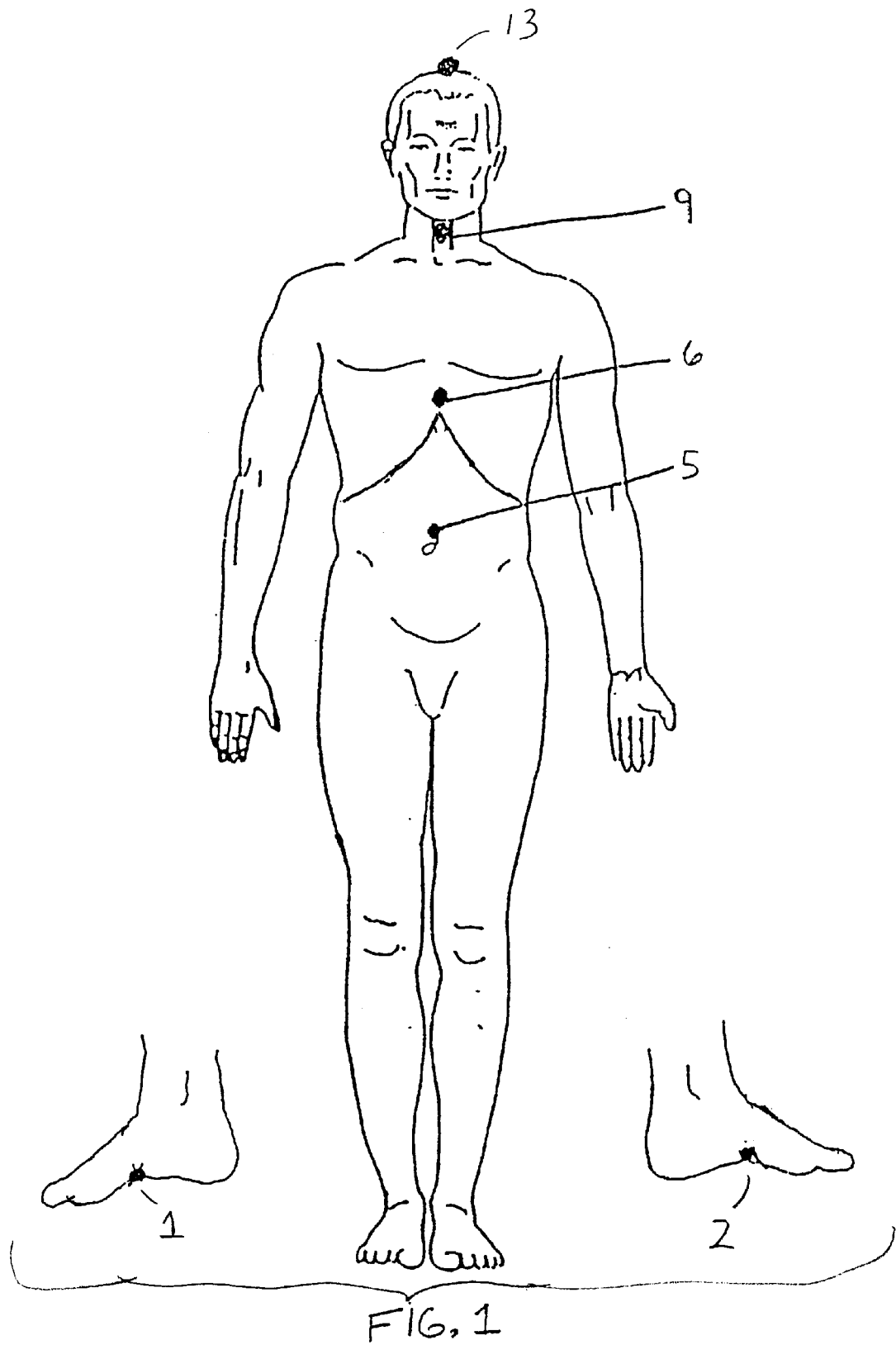
FIG. 1 is a frontal sketch of a human being illustrating six acupuncture points included in the Ring of Crystal.

In accordance with the present invention, antioxidant levels may be raised in human beings without the application of exogenous supplements of antioxidants or analogs. Stimulating biosynthesis of antioxidants within the body is advantageous over the heretofore known methods of raising antioxidants levels, which consisted of, for example, vitamin C, vitamin E, beta-carotene, taken either parenterally, intravenously, subcutaneously, or transdermally. In clinical studies of treatments involving their administration, antioxidants have been associated with undesirable side effects. These side effects include suppressing the elimination of cancerous and other life-threatening cells through apoptosis. Furthermore, some clinical studies have found that vitamin E can have some pro-oxidant activity, and excess supplementation could actually increase free radical activity. These and other side effects from the ingestion of antioxidants, and other undesirable consequences involving an exogenous method of antioxidant administration, can be avoided with the method of the present invention. No side effects have been detected from using the present invention to raise antioxidant levels in patients' blood.

To illustrate performance of the method of the present invention, an apparatus may be used as described in U.S. Pat. No. 5,109,847, the disclosure of which is incorporated by reference. Such apparatus has previously been used to increase serum dehydroepiandrosterone (DHEA) levels in patients by placing electrodes at particular points on an individual's body, specifically, Ring of Fire acupuncture points. See U.S. Pat. No. 5,609,617, the disclosure of which is also incorporated by reference. Such DHEA-enhancing electronic stimulation is preferably performed for 5 minutes for a period of days at each point on the body where the electrodes are placed. Such apparatus has also previously been used to stimulate the increase of endogenous neurotensin levels by placing electrodes at particular points on an individual's body, specifically, at the Ring of Air acupuncture points. See U.S. Pat. No. 6,233,489, the disclosure of which is also incorporated by reference.

The method of the present invention is directed to the application of electrical stimulation using the foregoing apparatus to the Ring of Crystal acupuncture points to stimulate the increase of endogenous antioxidant levels. Free radical levels were found to be significantly decreased for a majority of subjects after two to four days of this treatment. In one embodiment for carrying out the invention, a time-varying electrical potential stimulus is applied between a first electrode and a second electrode of the apparatus. The second electrode may comprise at least one means for making contact with a location on the subject proximate to a prescribed acupuncture point. Such electrical stimulus comprises a low-level voltage (typically yielding a current of less than 4 mA) pulse-train of relatively high frequency, i.e., between 12 kHz and 20 kHz, modulated in amplitude by a relatively low-frequency wave in the range of 8 Hz to 20 Hz. The low-frequency wave is preferably non-symmetrical, characterized by a 3:1 duty cycle, being "on" three-quarters and "off" one-quarter of the recurring period. By way of example only, the high-frequency pulses may occur at a 15 kHz rate at about a 4.0 mA level, while being subject to a 15 Hz modulation with a 3:1 duty factor.

Figure 3A:
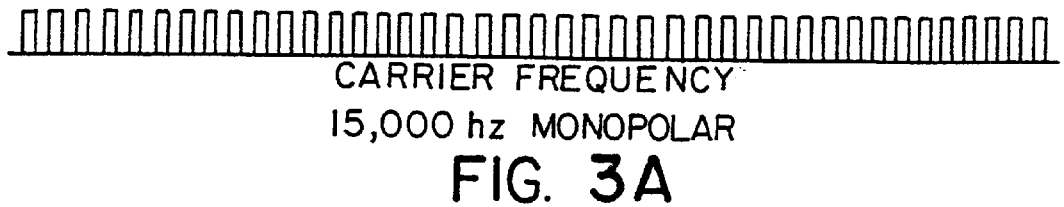
FIG. 3 are representations of stimulation waveforms that may be utilized in the present invention.
Figure 3D:
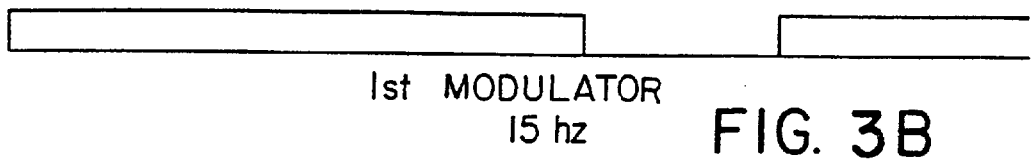
Figure 3D:
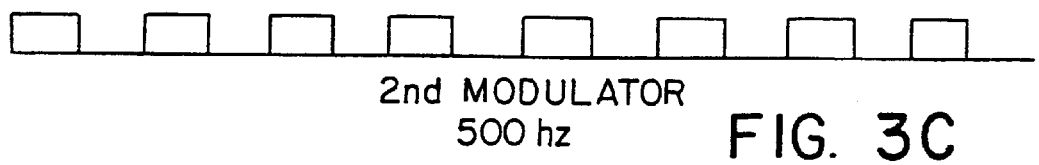
Figure 3D:
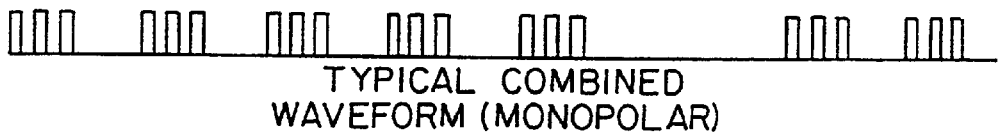

FIGS. 3A through 3E present the various components of the stimulus waveform in accordance with the invention. More particularly, FIG. 3A is a graphical representation of a carrier frequency signal for one specific time segment. In this example, the carrier frequency is 15 kHz with a duty cycle of 50%. FIG. 3B presents the first modulation to the carrier frequency. In this example, the first modulation has a frequency of 15 Hz in a duty cycle of 0.75. The second modulation is depicted in FIG. 3C. The second modulation has a frequency of 500 Hz and a 50% duty cycle. The waveform of the carrier frequency signal modulated by the signals of FIGS. 3B and 3C is shown in FIG. 3D (in simplified form) and contains 25 bursts of 15 pulses for each burst. The period for each burst is 2 ms and the period for each pulse is 66.7 μs. For each, the burst and the pulse, the duty cycle is 50% on time.

A cycle for the combined waveform will thus consist of 50 ms "on" time in which the pulses for that frequency combination are generated, and then an "off" time of 16.7 ms.

The complex waveforms of the present invention may be generated with sinusoidal, saw-tooth, hyperbolic, or other wave shapes; for clarity, the waveforms presented in FIG. 3, and further discussed below, have been exemplified by simple square wave.

Figure 3E:
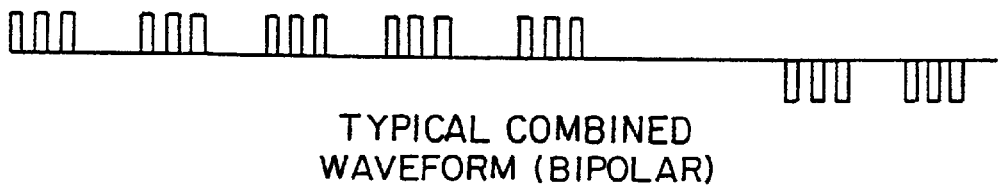

In FIG. 3E, an example of a complex waveform, according to the present invention, is provided wherein the polarity of the output is switched from positive to negative on a periodic basis, e.g., every 67 ms. This is contrasted with the waveform of FIG. 3D in which the polarity remains positive throughout the cycle; the pulsed DC waveform of FIG. 3D is considered a monopolar output while the output waveform depicted in FIG. 3E is considered bipolar.

For purposes of rough approximation, the energy dissipation in using an electrical stimulator according to the present invention is represented by the area under the pulses depicted in FIG. 3B. It can, therefore, be recognized that adding the second modulation, having a 50% duty cycle, results in a 50% decrease in power dissipation.

The stimulation circuit may provide any of the following exemplary frequency combinations (but is not limited to these):

1. 15 Hz, 500 Hz, 15,000 Hz-monopolar;
2. 15 Hz, 500 Hz, 15,000 Hz-bipolar (7.5 Hz);
3. 15 Hz, 500 Hz, 60,000 Hz-monopolar; or
4. 15 Hz, 500 Hz, 60,000 Hz-bipolar (7.5 Hz).

Figure 4:
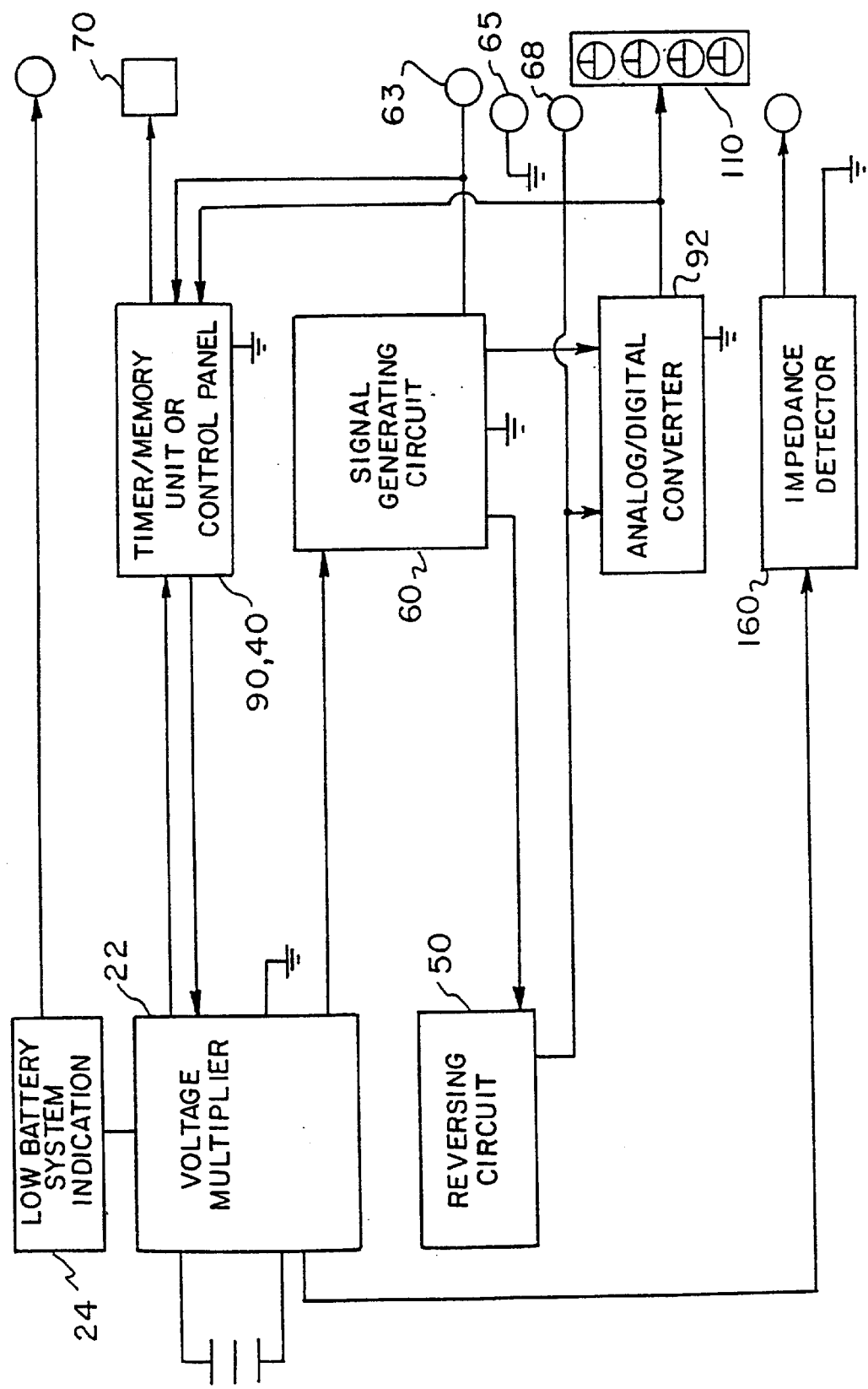
FIG. 4 is a block diagram of an apparatus for generating the stimulation waveforms depicted in FIG. 3.

FIG. 4 shows the functional elements an electrical stimulator system that may be used in the present invention. The power source to the electrical stimulator will either be a battery having, e.g., a nominal 9V terminal voltage or some rectified and properly transformed line (AC) power source. The battery provides the basic DC power source for generating the complex waveform. This is channeled and controlled by the voltage multiplier 22. The output of a voltage multiplier 22, which is typically between 27V to 40V, is fed to signal-generating circuits 60 which is the oscillating circuit that converts the constant DC output into the complex waveform having the desired characteristics.

The specific constant current and current-limited waveform generated by signal generating circuit 60 is pre-set by entering the various frequency settings for the two modulations and the carrier. This may be entered manually through adjusting the settings on control panel 90. Alternatively, these settings may be stored in digital memory 40 as previously set values. The actual output of this system is regulated by monitor 70 which then provides the system output on a display, via control panel 90, or a memory value for subsequent retrieval from digital memory 40.

The signal generating circuit 60 receives the output voltage from voltage multiplier 22. Within the signal generating circuit 60, the voltage branches off into a carrier frequency and two modulation frequencies. An example of the branching of the waveform is described in FIG. 3.

As shown in FIG. 4, the system supports two separate electrodes for placement on the patient. An electrode terminal 63 represents the positive terminal which receives the signal generated by the signal generating circuit 60. A second electrode terminal 65 is grounded within the circuit. For applying a bipolar stimulation waveform, the stimulation electrodes are connected to electrode terminals 65 and 68. The terminal 68 receives the output from a reversing circuit 50 which acts to flip the signal from the generating circuit 60 pursuant to preset timing constraints.

The following ancillary systems are also preferably present in the circuit. The low battery and system-on indicator 24 monitors the battery output via a voltage multiplier 22, and it generates an alarm signal when battery output voltage drops below a preset limit, for example, 7.0V. It also shuts the system down if the battery output voltage falls below a preset limit of approximately 6.0V.

The analog/digital converter 92 converts the signal from the signal generating circuit 60 so that the patient can read it. The analog/digital converter 92 senses the output voltage and converts it to an appropriate signal for the 4-gate integrated circuit which uses the signal to turn on the appropriate sequence of 4 LEDs 110. Finally, the impedance detector 160 is used to determine if the system is being used on a person (as opposed to someone just running the system without attaching it to a person).

Figure 5:
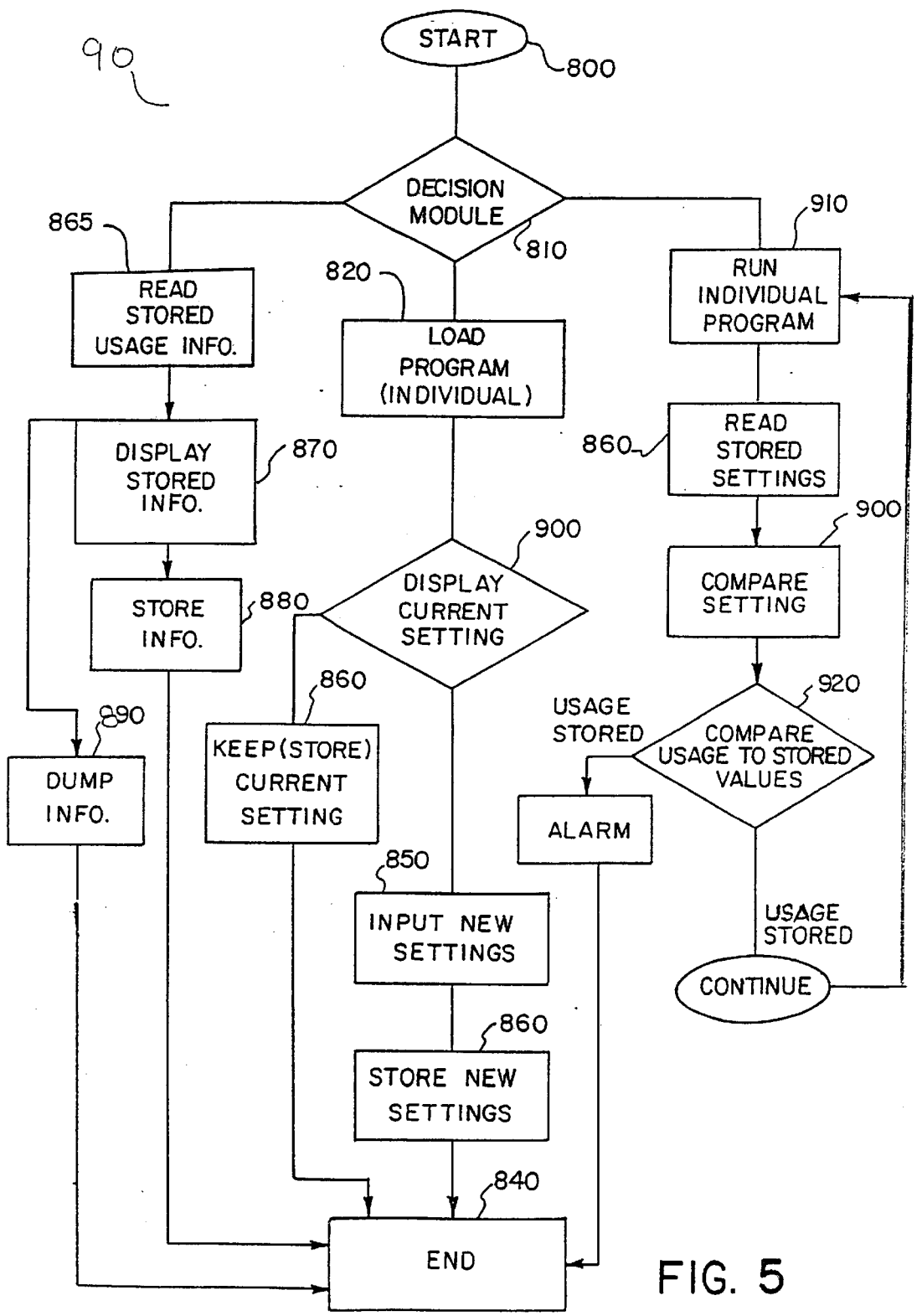
FIG. 5 is a logic flowchart of a data processing program controlling the operation of the apparatus of FIG. 4.

FIG. 5 is a flowchart of the operation of the timer unit 90 which the apparatus will use to monitor usage by the patient.

This program will prevent the patient from misusing the electrical stimulator apparatus and will allow the physician to set an individual treatment program and to monitor the patient's compliance to the set program. The timer unit 90 will allow the therapist to set the number of days this system is to be used, the number of times per day the system will be used, and the time duration for each use.

The program 800 starts with an Origination Decision Module 810. The Original Decision Module 810 will give the therapist three choices for use. If the Individualized Program 820 pathway is chosen, the timer unit will load the Individualized Program 820. Then the Individualized Program 820 will begin with a display showing the Current Setting 900 for each of the parameters (i.e., the number of days of use, the number of times per day of use, and the length of time for each use).

Next, the program will ask the therapist whether he or she wants to keep the current settings 855 or input new settings 850. If the therapist wishes to use the same settings as already registered in the program 800, the Individualized Program 820 will Store 860 the values and will End 840. However, if the therapist wishes to change the settings, the program will proceed to the Change Input Values 850 module in which the computer will ask the therapist for the new values for the settings. Then, the computer will Store 860 the new values and will End 840.

Another selection which a therapist may make at the Origination Decision Module 810 is to read the stored information from the patient's system. If the therapist decides to access the Read Stored Results 865 module, the Setting and Use information will be displayed 870 and the therapist will decide whether to store the patient information in the Patient Storage Module 880, or else it will dump the information 890 and it will End 840. A final selection which the therapist may access through the Origination Decision Module 810 is actually to use the system. Selecting this choice will initialize the Run Timed Program 910. The Run Timed Program 910 will read the Stored 860 values, then the program will Check 920 any Stored 860 values against the current run settings 900, which are the values of the Run Timed Program 910 for this usage of the system. If the current running settings 900 for the number of days of use is greater than the Stored 860 values, the program will End 840 without the system being turned on. Next, the Run Timed Program 910 will check the value of the Stored 860 values for the number of uses for a given date and, if the current running settings 900 are greater than the stored 860 values for the number of uses for a day, the system will End 840 for that day, and the system will not be able to be used until the next day. Finally, as the system is being used, a Running Time Clock will be compared to the Run Timed Program 910, and when the current running settings in 900 are greater than the Stored 860 values for the length of time for that session, the system will End 840 for that session, and the system will not be able to be used until the next session.

The LISS Cranial Stimulator (MEDIC Consultants, Inc., 265 Vreeland Avenue, Patterson, N.J.) is a commercially available device which provides an electrical signal equivalent to the corresponding signal described above. The device is the preferred electrical stimulator which produces a high-frequency electrical wave bearing a low-frequency amplitude modulation to a pair of electrodes used in the present invention.

A second exemplary apparatus that has been found to reduce free radical levels in human beings is the compact transcutaneous electrical nerve stimulator (Shealy TENS) described in U.S. Pat. No. 6,023,642 to Shealy, et al. This exemplary therapeutic device may be conveniently carried or worn by a patient. The output signal of the device includes a broad range of frequency components, extending into the GHz range, that may be provided to a patient via electrodes placed on the patient in appropriate locations.

Another form of electric stimulation of individuals has been found to decrease free radical levels in individuals. This stimulation may be applied by use of an apparatus capable of delivering a very high frequency electrical stimulus, e.g., up to 300 GHz at an energy level of up to 1 $\mu$V. This apparatus, referred to as a GigaTENS™ Electrical Stimulator, is used to provide the proper electrical stimulation to the individual to reduce free radical levels by placing the electrode from the device on specific points of an individual's body, and applying a very high frequency electrical stimulus, e.g., up to 30 GHz at a power level of $10^{-9}$ W/cm$^2$, and preferably at 52 to 78 GHz at an electrical power of $10^{-9}$ W/cm$^2$, in a sequential manner to a number of the specific points on the individual's body.

Figure 2:
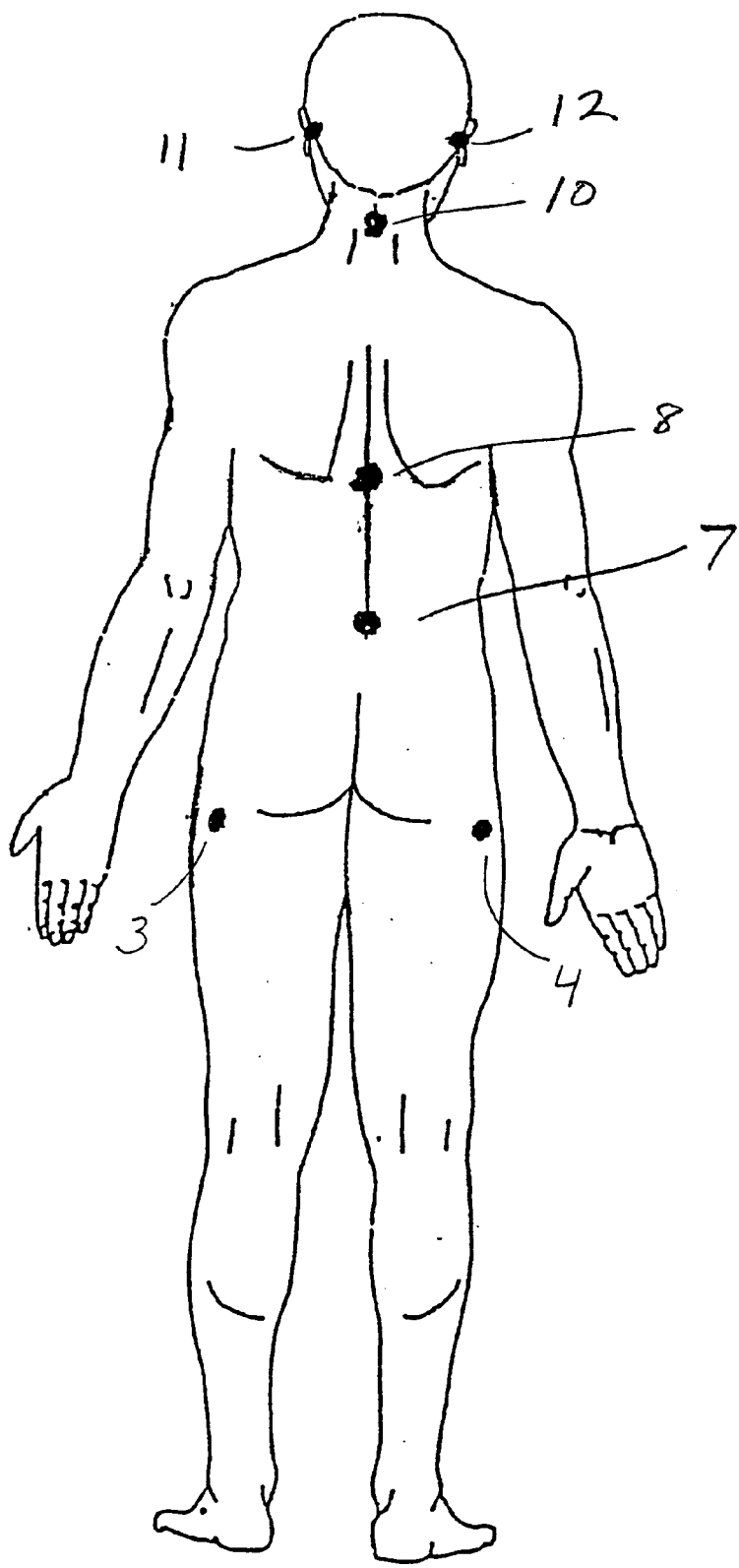
FIG. 2 is a back profile sketch of a human being illustrating seven acupuncture points included in the Ring of Crystal.

For the method of the present invention, these specific points on the individual's body correspond to 13 specific acupuncture points, hereinafter defined as the "Ring of Crystal." The Ring of Crystal points are located on the body as illustrated in FIGS. 1 and 2, and they correspond to the well-known acupuncture points of SP4, CV8.5, GV4.5, CV14.5, GV7.5, GV14.5, CV23, GV30.5, GB11, GV20. Generally, positions 1 and 2 are behind the ball and to the inside of the foot; positions 3 and 4 are in the crease of the buttock and to the side and slightly behind the hip; position 5 is right above the belly button; position 6 is at Lumbar Vertebra 2, located by drawing a line from position 5 around the body from the belly button to the spine; position 7 is located two finger widths above the Xiphoid process; position 8 is located by drawing a line around the body from the Xiphoid process to the spine at the thoracic vertebra 7; position 9 is the middle of Adam's apple; position 10 is located by drawing a line around the neck from the Adam's apple position to back of the neck on the spine; positions 11 and 12 are located above the mastoid bone (behind the upper part of the ear); and position 13 is the center top of the head. Although these acupuncture points are well known in Chinese acupuncture literature, it has been surprisingly and unexpectedly discovered in accordance with the invention that this combination of acupuncture points, i.e., the Ring of Crystal, can be electrically stimulated to reduce free radical levels in individuals.

Stimulation of the acupuncture points in accordance with the present invention may be carried out in a variety of sequences. One preferred method of carrying out the method of the present invention includes applying one electrode throughout the procedure at Governing Vessel 20 (GV20). Since the Shealy TENS is a monopolar stimulator, one preferred method is to place the negative electrode at GV20. For the bipolar LISS stimulator, the relative placement of its electrodes is immaterial. By way of example only, the contacts of the opposing electrode can be placed at pairs of acupuncture points beginning with points near the feet and sequentially stimulating points successively approaching the head. However, the present invention is not limited to any particular sequence.

When using the Shealy TENS or the Liss TENS stimulator, a preferred period of treatment at each acupuncture point is about 5 minutes, and the acupuncture points are preferably stimulated in pairs as described above. One electrode is preferably maintained continuously at GV20, and then the electrodes are applied in pairs to six pairs of the Ring of Crystal acupuncture points. When stimulating using the GigaTENS™, each acupuncture point is treated individually because the stimulation is applied at a single point through a single electrode. The preferred period of treatment using the GigaTENS™ is about three minutes at each acupuncture point.

The daily use of the stimulation method in accordance with the present invention was shown to be effective in many cases during the course of 2 to 4 days where, in some cases, daily stimulation over 4 days was interrupted by intervening weekend days. Thus, the treatment appears demonstrably effective with at least 2 days of stimulation and is foreseeably enhanced by daily stimulation over longer periods. Although a preferred minimum treatment period includes 2 treatments on consecutive days, a preferred long-term treatment regimen includes stimulation in accordance with the present invention preferably three or more times per week. This treatment may be applied indefinitely, since free radical production is a daily event.

In addition to lowering free radical levels, the method of the present invention may help to regulate the overall energetic system, assist in regulation, and treat certain neurological disorders, such as paralysis. Further alternative or derivative benefits of this present invention will be apparent to the practitioner of ordinary skill in the art.

The invention is further illustrated by the following exemplary research study which is not to be construed as limiting, but merely as an illustration of some preferred features of the invention.

EXAMPLE

The free radical levels of individuals participating in the study were initially determined prior to antioxidant enhancement by the present invention. For the results in Table 1, all free radical measurements of samples of urine taken from the subjects were performed using the VesPro Test Kit for Urinary Free Radicals (VesPro Life Sciences, LLC, 9716 Rosehill Road, Lenexa, Kans. 66215). VesPro's Free Radical Test™ is a urine test to monitor free radical activity and to assist the consumer in determining a more effective system of antioxidant therapy. It requires 1 mL of first morning urine into a reagent ampoule and a comparison after 5 minutes to a color gradient chart that indicates the amount of free radical activity in the test subject's body at a given point in time. The test uses urine malondialdehyde (MDA) measured by fluorometric and visually read calorimetric assay. It relies on the process of free radical production in the body producing certain chemical byproducts—one of which is MDA, a substance that produces the color reaction in the test. The test uses MDA as a biological marker useful to determine the optimal antioxidant supplementation level. The test is read on a 4-point scale from clear to pink, red and dark red, or 0, +1, +2 and +3. Zero suggests "possible low electron potential," 1+ is low oxidation, 2+ moderate, and 3+ heavy oxidation. Although the test kit suggests that the test be performed in a fasting state, no significant differences were detected among individuals tested at various times throughout a day. These free radical measurements are believed to be accurate to within +/−10%.

As shown in Table 1, 23 subjects, 10 females and 13 males, ranging in age from 21 to 72, volunteered for this study. A urine sample was taken to measure baseline free radical activity. The subjects then received electrical stimulation from one of two different TENS devices, the Liss TENS and the Shealy TENS, to the 13 acupuncture points identified as the Ring of Crystal. Electrical stimulation was applied in each case between an electrode at GV20 and a pair of electrically connected electrodes placed sequentially at six pairs of points corresponding to (referring to FIGS. 1 and 2) positions and 1 and 2, positions 3 and 4, positions 5 and 6, positions 7 and 8, positions 9 and 10, and positions 11 and 12. Each pair of points was stimulated with respect to the electrode at GV20 for 5 minutes, for a total of 30 minutes of stimulation. This procedure was repeated daily for between 2 to 4 days. The Liss TENS Cranial Stimulator was used with 16 subjects in the study and the Shealy TENS was used on the remaining subjects. The results of this study are shown in Table 1.

TABLE 1

Reduction of Free Radical Levels via Application of Electrical Stimulator to the Ring of Crystal Urinary Malondialdehyde (0 to 3 scale)

| Test Subject | Sex | Age | Baseline | Post Stimulation | Stimulator |
|---|---|---|---|---|---|
| 1 | F | 41 | 2.5 | 0 | Shealy TENS |
| 2 | M | 63 | 1.5 | 0.5 | Shealy TENS |
| 3 | F | 49 | 1.5 | 0.5 | LISS |
| 4 | F | 20 | 3 | 2 | Shealy TENS |
| 5 | F | 50 | 3 | 0 | Shealy TENS |
| 6 | F | 48 | 2 | 0 | LISS |
| 7 | M | 60 | 2 | 2 | LISS |
| 8 | M | 26 | 1 | 0 | LISS |
| 9 | F | 72 | 1 | 0 | LISS |
| 10 | M | 55 | 2 | 1 | LISS |
| 11 | F | 60 | 1 | 0 | LISS |
| 12 | M | 40 | 2 | 0 | LISS |
| 13 | F | 21 | 3 | 3 | LISS |
| 14 | M | 69 | 3 | 0 | Shealy TENS |
| 15 | F | 45 | 3 | 0 | LISS |
| 16 | M | 42 | 1 | 0 | LISS |
| 17 | M | 47 | 1 | 0 | LISS |
| 18 | M | 38 | 1.5 | 0.5 | Shealy TENS |
| 19 | M | 51 | 2.5 | 1.0 | LISS |
| 20 | M | 55 | 3 | 0.5 | LISS |
| 21 | F | 50 | 2 | 0 | LISS |
| 22 | M | 27 | 3 | 3 | LISS |
| 23 | M | 53 | 1.5 | 0.5 | Shealy TENS |

Overall, the subjects showed a 78.6% decrease in free radical activity over the course of the test period. Of the 23 subjects, 20 showed a decrease in free radical activity over the course of the test period. Of these, 12 had no excess free radicals after stimulation.

Prior to the study, at least half of the subjects with excess free radicals had been taking significant oral antioxidants. But, some of the subjects with no urinary free radicals had not been taking antioxidant supplements.

The three subjects who experienced no reduction in free radicals were treated using only the LISS TENS. However, test subject No. 14, who initially exhibited no effect from the LISS TENS, responded well to the Shealy TENS. Ideally, then, those who do not respond to the LISS TENS should also try the Shealy TENS. This is consistent with findings of an earlier study that higher frequencies are necessary to treat some individuals. See Shealy, et al., "Electrical stimulation raises DHEA and improves diabetic neuropathy," *Stress Medicine*, Vol. (11), pp. 215–217 (1995).

To verify the accuracy of the MDA urine test, test subjects Nos. 1–5 also had blood drawn before and after the stimulation. The blood serum was frozen and sent to MediMetrix Clinical Laboratory in Norcross, Ga. for measurement of lipid peroxidase. The results are detailed in Table 2.

TABLE 2

Lipid Peroxidase (nanomols/ml)

| Test Subject | Sex | Age | Baseline | Post Stimulation | Stimulator |
|---|---|---|---|---|---|
| 1 | F | 41 | 1.2 | 0.9 | Shealy TENS |
| 2 | M | 63 | 1.2 | 1.0 | Shealy TENS |
| 3 | F | 49 | 0.8 | 0.8 | LISS |
| 4 | F | 20 | 1.2 | 1.0 | Shealy TENS |
| 5 | F | 50 | 1.6 | 1.3 | Shealy TENS |

The normal range for lipid peroxidase is up to 1.0 nanomols/ml. After the stimulation, all four of the test subjects in Table 2 who had elevated lipid peroxidase baseline levels experienced reductions; three of them fell into the normal range.

Although the less expensive VesPro™ urinary test appears to be somewhat sensitive, the confirming results of the lipid peroxidase tests provide high confidence in the results of the study using the urine tests.

The present invention may be embodied in other specific forms without departing from its spirit or its central characteristics. The described embodiments are to be considered in all respects only as illustrative and not restrictive. The scope of the invention is, therefore, indicated by the following claims, rather than by the foregoing description. All changes which come within the meaning and range of equivalency of the claims are to be embraced within their scope.

What is claimed is:

1. A method of reducing free radical levels in an individual comprising the steps of:
   (a) applying electrodes sequentially to at least one selected Ring of Crystal acupuncture point of the individual's body other than the GV20 acupuncture point; and
   (b) applying a high-frequency of at least 1 kHz electrical stimulus bearing a low-frequency amplitude modulation to the electrodes at each selected acupuncture point repetitively over a period of time sufficient to result in stimulation of endogenous production of antioxidants within the individual.

2. The method of claim 1 wherein the electrical stimulation is applied for a period of time of approximately five minutes at each selected acupuncture point at least once per day over a period of at least two days.

3. The method of claim 1 wherein the frequency of the high-frequency electrical stimulation is in the range of 12 to 20 kHz, the low-frequency amplitude modulation is in the range of 8 to 20 Hz, and wherein the current applied to the individual by the electrical stimulation does not exceed about 4.0 mA.

4. The method of claim 3 wherein the amplitude of the modulation is non-symmetrical.

5. A method of reducing free radical levels in an individual comprising the steps of:
   (a) applying an electrode sequentially to at least one selected Ring of Crystal acupuncture point of the individual's body other than the GV20 acupuncture point; and
   (b) applying an electrical stimulus have a frequency of 52 to 78 GHz at a power level of about $10^{-9}$ W/cm$^2$ to the electrode at each selected acupuncture point repetitively over a period of time sufficient to result in stimulation of endogenous production of antioxidants within the individual.

6. The method of claim 5 wherein the electrical stimulation is applied for a period of time of approximately three minutes at each selected acupuncture point.

7. A method of reducing free radical levels in an individual comprising the steps of:
   (a) applying a first electrode sequentially to at least one selected Ring of Crystal acupuncture point of an individual's body;
   (b) applying a high-frequency electrical stimulus bearing a low-frequency amplitude modulation to the first electrode at each selected acupuncture point;
   (c) applying a second electrode sequentially to at least one other selected Ring of Crystal acupuncture point of the individual's body;
   (d) applying a high-frequency electrical stimulus to the second electrode at each selected acupuncture point; and
   (e) repeating steps (a) through (d) repetitively over a period of time sufficient to result in stimulation of endogenous production of antioxidants within the individual.

8. The method of claim 7, wherein steps (a) through (d) are repeated on each Ring of Crystal acupuncture point of the individual's body, and the high-frequency electrical stimulus is applied for about five minutes at each Ring of Crystal acupuncture point.

9. A method of reducing free radical levels in an individual comprising the steps of:
   (a) applying an electrode sequentially to at least one selected Ring of Crystal acupuncture point of an individual's body other than the GV20 acupuncture point;
   (b) applying a high-frequency electrical stimulus to the electrode at each acupuncture point; and
   (c) repeating steps (a) through (b) repetitively over a period of time sufficient to result in stimulation of endogenous production of antioxidants within the individual, wherein steps (a) through (b) are repeated daily over a period of at least two days, and wherein the high-frequency electrical stimulus is conducted for a period of about three minutes using an electrical stimulator delivering up to 300 GHz at an electrical power up to about $10^{-9}$ W/cm$^2$.

10. A method of reducing free radical levels in an individual comprising the steps of;
    (a) applying electrodes, the electrodes attached to an electrical generator, to Ring of Crystal acupuncture points sequentially at each of the acupuncture points; and
    (b) applying an electrical stimulus to the electrodes from the electrical generator, the stimulus having a moderately high-frequency of at least 1 kHz and an electrical amplitude which does not exceed 2 mA, to stimulate endogenous production of antioxidants within the individual.

11. The method of claim 10 wherein the step of applying the electrical stimulus further comprises applying the electrical stimulus for a period of about 5 minutes to the electrodes.

12. A method of reducing free radical levels in an individual comprising the steps of:
    (a) applying electrodes sequentially to at least one selected Ring of Crystal acupuncture point on an individual's body other than the GV20 acupuncture point;
    (b) applying an electrical stimulus having a frequency of 52 to 300 GHz sequentially to the electrodes at each of the selected Ring of Crystal acupuncture points; and
    (c) continuing electrical stimulus for approximately three minutes at each point to stimulate endogenous production of antioxidants within the individual.

13. The method of claim 12 wherein the amplitude of the electrical stimulus does not exceed 1 $\mu$V at any one acupuncture point.

* * * * *